US008959982B2

(12) United States Patent
Pearce et al.

(10) Patent No.: US 8,959,982 B2
(45) Date of Patent: Feb. 24, 2015

(54) DYNAMIC CANINE TRACKING METHOD FOR HAZARDOUS AND ILLICIT SUBSTANCES

(71) Applicant: Auburn University, Auburn, AL (US)

(72) Inventors: John Pearce, Jacksonville, AL (US); L. Paul Waggoner, Jacksonville, AL (US); Jeanne S. Brock, Ft. McClellan, AL (US); Timothy Baird, Jacksonville, AL (US); David A. Baffa, Piedmont, AL (US); Daniel McAfee, Piedmont, AL (US); Robert E. Leonard, Weaver, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 14/141,199

(22) Filed: Dec. 26, 2013

(65) Prior Publication Data

US 2014/0102380 A1    Apr. 17, 2014

Related U.S. Application Data

(62) Division of application No. 12/870,732, filed on Aug. 27, 2010.

(60) Provisional application No. 61/240,049, filed on Sep. 4, 2009.

(51) Int. Cl.
| | | |
|---|---|---|
| *G01N 33/22* | (2006.01) | |
| *A01K 15/00* | (2006.01) | |
| *A01K 15/02* | (2006.01) | |
| *F41H 11/132* | (2011.01) | |
| *F41H 13/00* | (2006.01) | |

(52) U.S. Cl.
CPC ............... *A01K 15/00* (2013.01); *A01K 15/02* (2013.01); *F41H 11/132* (2013.01); *F41H 13/00* (2013.01)

USPC ................ 73/23.34; 119/712; 119/174

(58) Field of Classification Search
USPC ............... 119/417, 420, 421, 174, 905, 712; 73/23.34, 23.2, 23.4, 23.42, 864.33, 73/865.8

See application file for complete search history.

(56) References Cited

U.S. PATENT DOCUMENTS

| | | | |
|---|---|---|---|
| 6,843,158 B2 | 1/2005 | Garcia et al. | |
| 6,923,079 B1 * | 8/2005 | Snibbe | ............ 73/866.1 |
| 6,979,298 B2 | 12/2005 | Vodyanoy et al. | |
| 7,188,513 B2 * | 3/2007 | Wilson | ............ 73/31.05 |
| 8,547,237 B2 * | 10/2013 | Adebimpe | ............ 340/573.2 |
| 2001/0047771 A1 * | 12/2001 | Bulanda et al. | ............ 119/712 |
| 2008/0163671 A1 * | 7/2008 | Dugan | ............ 73/23.34 |
| 2009/0038555 A1 * | 2/2009 | Reese | ............ 119/174 |
| 2009/0077908 A1 | 3/2009 | Brasfield | |
| 2009/0139459 A1 | 6/2009 | Habacivch et al. | |

* cited by examiner

Primary Examiner — Rob Swiatek
Assistant Examiner — Lisa Tsang
(74) Attorney, Agent, or Firm — Andrus Intellectual Property Law, LLP

(57) ABSTRACT

Vapor wake detection is a highly advantageous method and system for detecting explosives and other illicit substances. With vapor wake detection, a canine and a handler are used; however, unlike other detection schemes, the canine leads the handler. After the handler positions the canine in a desired location, the canine detects scents in the air that come to the canine. When the canine detects a trained scent, the canine leads the handler to or follows behind the carrier of the item with the scent. Once the carrier is identified by the handler, the proper personnel are contacted. To implement vapor wake detection effectively, specific rigorous training is utilized.

12 Claims, 3 Drawing Sheets

DYNAMIC CANINE TRACKING METHOD FOR HAZARDOUS AND ILLICIT SUBSTANCES

CROSS-REFERENCE TO RELATED APPLICATION(S)

This application is a divisional of U.S. patent application Ser. No. 12/870,732, filed Aug. 27, 2010, which application was published on May 10, 2012, as US2012/0111285. Said application further claims priority under 35 U.S.C. 119(e) of the U.S. Provisional Patent Application Ser. No. 61/240,049, filed Sep. 4, 2009, and entitled, "DYNAMIC CANINE TRACKING METHOD FOR HAZARDOUS AND ILLICIT SUBSTANCES," the contents of which are hereby incorporated by reference in their entireties for all purposes.

FIELD OF THE INVENTION

The present invention relates to the field of substance, material and object detection. More specifically, the present invention relates to detection of hazardous or illicit substances, materials or objects using a canine.

BACKGROUND OF THE INVENTION

Drug sniffing dogs have been utilized for many years in areas such as ports and airports to sniff for and locate illegal drugs. A handler leads the dog to each container or luggage, and the dog attempts to pick up a scent of any drugs. The handler is the one who directs the search and the dog is merely used as a sniffing mechanism. The dog searches the target (a person, a vehicle, luggage, a warehouse, etc.) for any odor it has been trained to recognize and gives the handler a final response if any such odor is detected.

Similarly, bomb sniffing dogs have been utilized at airports and other locations to sniff for and locate bomb devices. Again, a handler guides the dog to search luggage and other items and locations. These techniques are very simplistic and have many flaws.

Although many explosives and thousands of pounds of drugs have been uncovered in this manner, "handler driven" canine detection has some disadvantages. One disadvantage is the narrowness of the search. For example, if the handler does not stop every single person walking through an airport to let the dog search them for explosives, then the dog may miss a person carrying a bomb under his shirt. The dog can only search those targets that the handler instructs the dog to search. In other words, the dog only gets to search those targets that the handler deems are necessary to search. Another disadvantage is the obtrusiveness of the search. It is very obvious that officers are searching for something if a handler is leading a dog around while pointing to things for the dog to sniff.

SUMMARY OF THE INVENTION

Vapor wake detection is a highly advantageous method and system for detecting explosives and other illicit substances. With vapor wake detection, a canine and a handler are used; however, unlike other detection schemes, the canine leads the handler. After the handler positions the canine in a desired location, the canine detects scents in the air that come to the canine. When the canine detects a trained scent, the canine leads the handler to or follows behind the carrier of the item with the scent. Once the carrier is identified by the handler, the proper personnel are contacted. To implement vapor wake detection effectively, specific rigorous training is utilized.

In one aspect, a dog-driven detection method of detecting hazardous or illicit substances, comprises detecting a source of a target odor and leading a handler to the source of the target odor via a canine, wherein the source of the target odor comes within a detectable range of the canine. The canine searches the air for vapor trails or scent pools of the target odor generated by a moving or stationary target. The canine accommodates dissipation of the target odor over time.

In another aspect, a method of training canines to carry out detection, wherein the canines are chosen based on a canine selection process comprises choosing canines that are motivated to sniff and search independently in a manner to disguise their handlers, documenting the canines' sniffing capabilities and choosing healthy canines that pass medical examinations. The method further comprises choosing canines that are not overly sociable. The medical examinations include testing for dexterity and freedom from bone, joint and musculature pathologies.

In another aspect, a method of training a canine for detection, the method comprises choosing a detector canine that demonstrates a high level of independent search behavior, teaching the canine that the source of a target odor is not limited to stationary objects, teaching the canine to follow a vapor-wake of a moving target, teaching the canine to sample air currents and teaching the canine to follow the vapor-wake to the target and give a final response.

In yet another aspect, a method of implementing vapor wake detection comprises positioning a canine, detecting a target odor, recognizing the canine's change of behavior when the target odor is detected, identifying a carrier of an item emitting the target odor and notifying security personnel of the carrier. Positioning the canine depends on a location type and air currents throughout a location. The location type is selected from the group consisting of a choke point, a crowd, people standing in line, people moving and people standing still. The method further comprising manipulating the air currents using an air manipulation device. The change in behavior includes following the carrier from behind at a distance determined by a handler. The target odor is selected from the groups consisting of an explosive and an illicit substance.

In yet another aspect, a system for implementing vapor wake detection comprises a canine for detecting a target odor and following a carrier of an item emitting the target odor and a handler for positioning the canine, recognizing a change in behavior of the canine, identifying the carrier and notifying security personnel of the carrier. Positioning the canine depends on a location type and air currents throughout a location. The location type is selected from the group consisting of a choke point, a crowd, people standing in line, people moving and people standing still. The air currents are manipulated using an air manipulation device. The change in behavior includes following the carrier from behind at a distance determined by a handler. The target odor is selected from the groups consisting of an explosive and an illicit substance.

DETAILED DESCRIPTION OF THE PREFERRED EMBODIMENT

Figure 1:
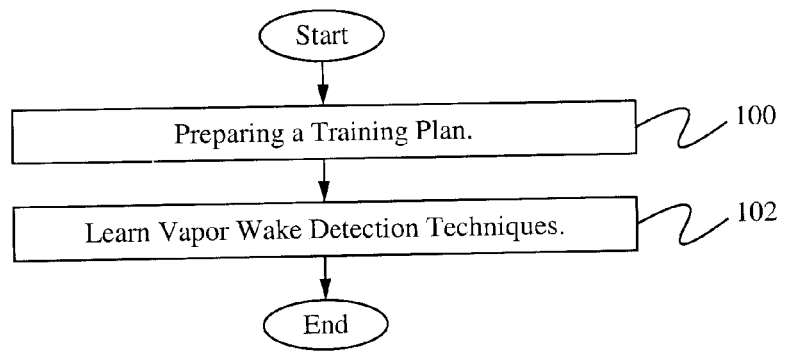
FIG. 1 illustrates a flowchart of a method of training a team in vapor wake detection according to some embodiments.

A method of detection of or person-screening of hand-carried and/or body-worn hazardous or illicit substances, materials or objects in dynamic environments is described. The method is a novel "dog-driven" detection method which is distinguished from traditional canine detection methods which are "handler driven." In this manner, a sniffing target comes to the dog (usually on a lead) rather than the dog going to the sniffing target.

A method of canine interrogation and detection of the vapor or volatiles wake emanating from persons is described. The method is referred to as Vapor-wake Detection. Some features of this method include the ability to 1) screen large numbers of persons passing through a given space without affecting the throughput of the persons through the space; 2) a specific dog deployment strategy; 3) dogs are able to accommodate dissipation or decay of target odor over time; and 4) dogs are able to overcome distractions such as noise, commotion and ancillary environmental odors, to prevent loss of tracking of the target odorant.

A method of training dogs to carry out Vapor-wake Detection is described. The method includes a canine selection process containing the following selection criteria: 1) documented sniffing capability (dogs trained to sniff selected targets; 2) healthy dogs capable of passing medical examination including dexterity, freedom from bone, joint and musculature pathologies; 3) not overly sociable animals; 4) motivated to sniff and search independently and in a non-obvious manner to disguise handler (handler takes over once a person has been identified); and 5) a manual for dog maintenance and conditioning for the ultimate dog handler.

The method of canine training also includes a procedure/protocol for training which includes specific steps including 1) modulating behavioral aspects such as aggressiveness; 2) maneuvering around various obstacles and distractions during the screening/detection process; and 3) operation in high human density environments.

Applications of the methodology include the interdiction and capture of suicide bombers, narcotics handlers and purveyors of illicit chemical/biological warfare materials. The methodology is able to be applied in varied environments such as transit systems, venues for large public event gatherings such as stadiums and buildings, areas of commerce such as shopping malls and military environments.

Vapor Wake Detection Canines

A vapor wake detection canine is a detector dog with formal training to indicate a trained substance carried on or worn by a person. The canine is non-aggressive towards people, pets and other harmless objects. The vapor wake detection canine is worked on-leash. In particular, the vapor wake detection canine is able to analyze a vapor wake which is a path or course a target has taken, leaving behind an invisible suspension in the air of odor emitted from the target.

A handler assesses air currents/movement in the search area (e.g. predetermined boundaries within which the dog operates) and ensures the canine has access to productive areas (e.g. specific locations in a search area that provide the dog higher probability to encounter the substance odor), determined by air currents/movement. The handler does not influence the canine once the canine has initially encountered the substance odor. The canine searches independently of the handler—without guidance or direction to work differential thresholds to target. The canine is specifically searching the air for the substance odor vapor trails and/or scent pools generated by a moving or stationary target. The target is the location from which the odor originates. The canine is not searching people. The canine's deployment is adaptable to various environments to include but not be limited to stationary checkpoints, crowds, moving lines of people and any area of pedestrian activity.

Vapor wake training begins with a detector dog that demonstrates a high level of independent search behavior (e.g. a dog's capability to perform without assistance or being influenced by a handler). The canine learns the source of the target odor is not limited to stationary objects. The canine learns to follow a moving target. Following a moving target includes: upon identifying a moving target, the dog pursues the target from behind, at a distance determined by the handler. The canine learns to sample air currents. The canine learns to follow the vapor-wake to the target and give a final response (e.g. a behavior that a dog has been trained to exhibit in the presence of a target odor source such as sitting).

Vapor Wake Screening

When a canine team is screening people, if the handler is dressed in uniform, the team serves as a very valuable deterrent to explosives and contraband being carried into an area. Or, if the vapor wake screening is to be conducted in a less apparent manner, the handler is able to be in street clothes, appearing to be walking a pet dog or a service dog for the handicapped.

During vapor wake screening activities, the canine detects an explosive odor, but the handler is important to the process. The handler positions the canine in an area that compliments vapor wake screening, and in particular, the types of vapor wake screening to be conducted. The team is trained to detect explosives in different scenarios, including, but not limited to, areas in which people are walking or standing, lines of people and crowds in which people are standing or moving.

If explosive odor is detected while air screening, the canine is trained to follow behind the perpetrator or approach a non-moving perpetrator from behind. Upon recognizing the canine's change in behavior (e.g. a characteristic pattern of behaviors as interpreted by the handler that occurs when the dog detects a trained odor) and identifying the person carrying explosives, the handler should remove the canine from the area as to not alert the perpetrator. This is able to be done any time before the canine begins the final response (sit). The handler then discreetly notifies other security personnel so they are able to covertly approach or follow and observe the perpetrator to take further action in accordance with agency standard operating procedures.

Choke Points

This is a very effective way to screen people for explosives. The canine is allowed to freely move side-to-side within the choke point, without interfering or making physical contact with persons passing through the choke point. This utilizes good leash manipulation by the handler. The canine becomes increasingly more effective as the width of the choke point narrows. As pedestrians walk past the canine, the canine is cast at leash length behind the person or group of people as the handler maintains a loose static position. The vapor wake screening dogs are trained to sample the plume of air coming off the person's body as they walk past the team.

Crowds

Screening of crowds is conducted throughout an area. This is more difficult than at a choke point but is achievable for the canine team. The handler is conscious of air currents; however, these currents become more disturbed with the movement within the crowd. The handler utilizes leash manipulation to navigate the canine through and around the people forming the crowd.

If the crowd is moving in a certain direction, the canine should be cast from side-to-side behind the crowd while moving in the same direction. This requires the handler to move from side-to-side to allow the canine to sample the plume of air coming off the individuals.

If the crowd of people is moving various directions, the handler takes advantage of available air currents while moving the canine in and out of the crowd to air scent in all directions.

If the crowd is standing still, the handler moves to the downwind flank of the crowd and discretely begins to move the canine into the crowd in a quartering fashion.

People Standing in Line

If the team is to screen people standing in line, a screening point or choke point where the line of people must pass by the canine team should be established. When necessary to screen an established line of people, the handler first evaluates existing air currents in determining the best way to conduct the screening. The best scenario to screen people standing in line is to have an air current perpendicular to the direction of the line. The handler would then move the canine in the direction of the line while staying on the downwind side of the line.

When the air current is moving in the direction of the line, the handler begins downwind of the line. As the team approaches the line, the handler moves the canine close to the people in the direction of the line, occasionally moving through the line to the other side and then again in the direction of the line.

Manipulation of Air Currents

A very important factor the handler should fully understand about positioning the canine properly is direction of air currents. This is a constant process since air current direction is able to change with changes in the environment. Factors which affect air currents include, as examples, air vents, arrivals and departures of various large transportation conveyances and the opening and/or closing of doors and/or windows. Canines trained are able to be used with natural air currents in the environment within which the team is working or with manipulated wind currents.

Fan(s), or other air current manipulators, while not a necessity, are able to be utilized to establish air currents which assist the canine in detecting explosive odor. The fans are positioned at predetermined distances from the area the canine is to be utilized. Fan placement is made to produce a light breeze toward the canine team. A hard or fast breeze will reduce the width of the scent cone and lessen the canine's capability. The direction of the breeze is determined by the performance of the team during training while using the fans. Therefore, the following are possible fan placements in various operational settings.

Choke Points

As pedestrians pass through a choke point, a fan is placed so a light breeze is blowing into the face of the people passing though the choke point. As people pass by the canine team, the handler casts the canine behind the people, positioning the canine downwind of the people moving through the choke point.

Crowds

When screening is conducted through a crowded area, fan(s) are placed on the perimeter of the area to establish a light breeze. The team begins screening the area at the farthest point of the area, downwind of the crowd. The team quarters the area. The team moves in and out of the crowd while quartering upwind. The handler at all times maintains an awareness of the teams position in relation to the air currents.

People Standing in Line

When screening people standing in line, fan(s) are placed in a position to generate a light breeze perpendicular to the line of people. The team then moves up and down the line of people while remaining downwind of the line.

Maintenance/Proficiency Training

Objective-oriented training is planned before each training session to maintain and advance the canine's current level of proficiency. Vapor wake screening training is conducted with more focus on the canine because the canine is air scenting and works very independently. Therefore, it is acceptable for the handler to be knowledgeable of the person acting as the training perpetrator in earlier stages of training Eventually, however, the training is conducted without the handler knowing the location or the training perpetrator. During training, the handler continually analyzes the canine's behavior. Upon recognizing the canine's change of behavior to explosive odor, the handler allows the canine to follow the training perpetrator. The handler maintains a taut leash and allows the canine to pull with considerable force. The handler maintains a distance from the training perpetrator and this distance is able to be increased through successive approximation during training; however, the handler should not run with the canine. The canine is allowed to continue to follow the training perpetrator carrying the training aid until the perpetrator comes to a complete stop. Upon the training perpetrator coming to a complete stop, the canine should give the final response of "sit" a few feet behind the perpetrator. After a pre-determined time, the training perpetrator turns around to face the dog, removes the hidden reward, and tosses the reward directly to the dog's mouth. In some embodiments, the training is not conducted until the following variables are fully planned:

1. The type of explosives training aid to be used.
2. How the training aid is to be carried or packaged.
3. The type of vapor wake screening to be conducted.
4. Air currents (natural or manipulated) and their direction.
5. The amount of time before or between exposure to explosive odor.
6. The direction and route the person carrying the explosives is to take.
7. The number of times the canine gives a final response and/or the time the dog remains in the final response before being rewarded.
8. Distracters to be used during the training.

Explosive Training Aids

All explosive training aids the canine is trained to detect should be used, at different times, when conducting maintenance/proficiency training Care is taken in storage and handling of explosive training aids used in vapor wake screening to prevent cross-contamination of training aids. In addition, these training aids should be stored separately from training aids used in regular explosive detection training There is a likelihood that the training aids used in vapor wake screening will become contaminated with human odor since some of the training requires the placement of the aid being carried close to a person's body. However, every precaution should be taken to prevent such contamination, such as not allowing the training aid to ever make direct contact with a human. The training aid should be wrapped in barrier material to prevent human contamination.

When conducting vapor wake screening, the type of explosives and quantity should be varied so the canine remains proficient at detecting all the different types of trained explosives odor and different quantities.

Training Aid Placement

Training aids are placed in items including, but not limited to, backpacks, rolling luggage, carried luggage, purses and packages. Any possibility is replicated, and the training perpetrator is able to look like any pedestrian or commuter. When replicating a suicide bomber, the use of a second-chance vest (after removing the body armor) works well and is covered with clothing. Additionally, a hunter's vest or jacket with interior pockets works well depending on the season.

During training, the amount of time the training aid is in place before training begins is varied. When training first begins with a new team, the training aid is in place at least 30 minutes prior to the canine encountering the explosive odor. This time is able to be slowly reduced using successive approximation. Eventually, the canine is capable of detecting explosives placed out for shorter amounts of time.

During vapor wake screening training, the canine is not able to cue visually off the training perpetrator by noticing unusual bulk or recognition of the person and/or baggage. Therefore, frequently new training perpetrators are used along with new baggage, backpacks, packages and garments. The same training perpetrator is able to be used several times during a training day, but once it is determined to change training perpetrators, the old training perpetrator departs the area. The canine should not encounter this person even outside of training until after the person has bathed and changed clothes to remove all explosives odor, especially when replicating a suicide bomber scenario.

Training the Vapor Wake Screening Team

Again, planning is important to good objective-oriented training sessions. Prior planning ensures the training objective is achieved and increases the canine's proficiency. The type of vapor wake screening training varies between choke point, crowds and people moving and/or standing still through the canine's working life. Prior to training, determine where and how the canine works the training scenario. Air currents are determined throughout the area in which the canine team is working. This is to include the training perpetrator's entire route of travel. It is also determined if any air currents are to be manipulated with the use of fan(s).

When conducting training, extension of the time in which the canine is capable of effective vapor wake screening is done by using successive approximation. Good documentation of training sessions and a strong objective-oriented training program is essential to achieving this objective. Variation of time before encountering explosive odor, from the shortest to the longest times achieved in training, is important. If training always is consistent with a certain amount of time, the canine begins to anticipate this time and not search during other periods of time. Occasionally, extending the longest time searched, by adding a couple of minutes before the canine encounters explosive odor, is beneficial. As long as the canine is successful, continue to occasionally extend the time is helpful, but variation of the search time is more important to the success of the canine's capability.

While doing vapor wake screening training, support from various people to perform the role as the training perpetrator is used. Enlisting a variety of people to perform this function, utilizing various sizes, races, males and females is beneficial. Since inevitably the person used will not be familiar with vapor wake screening, canine training, or even dogs in some cases, precise instructions should be given to ensure proper behavior and performance. They should understand the following:

1. If they are moving, the should know where to position themselves in a crowd of people and how close to come to the canine as they move through a choke point or area.

2. After they walk past the canine, they should know the precise direction of travel, exact route to take.

Additionally, they should understand if at any time they are to stop and how soon they should remain still before moving again, and then the final location they should stop at. Upon stopping they should understand how long they should remain still before they turn 180 degrees, face the canine, remove the canine's reward and toss the reward directly to the canine's mouth. During training, the number of stops the perpetrator makes before stopping at the reward stop should be varied. Additionally, various paces for the canine to follow should be used, from a slow walking pace to a run. This is the only time the handler is allowed to run with the canine; however, the handler should still maintain a taut leash for better leash manipulation and control.

Use of Distraction

Vapor wake screening canine's ability to work around distractions, ignore them and remain focused on the task is only able to be achieved if proper objective oriented training is conducted. One distraction that is incorporated into training is the blank (non-explosive carrying) or non-perpetrator actor carrying the canine reward. This actor is able to carry several reward objects simultaneously to enhance the opportunity to see if the canine is prone to exhibit an interest that is able to be confused with explosive training aid detection, especially early in operational training. These actors and the reward objects they carry are carefully staged/handled to ensure they do not inadvertently contact explosive odor. Quarantining all potential "other odor" distractions (e.g. food) from explosive training aids is important.

Non-odor-based distractions include all of the probable sights, sounds and circumstances the canine is able to encounter and will effectively work around in its operational mission. Distractions include people blocking the canine's path as it follows the training perpetrator, or having someone attempt to pet or physically distract the canine while it is following a training perpetrator or working explosive odor. As with any environmental conditioning of a canine, intense, sudden or otherwise potentially startle or fear inducing stimuli should be introduced through careful gradual exposure and successive approximations to approaching the stimuli. The greater the variety of potential distractions to which the dog is conditioned, the more likely the dog is going to handle novel distractions it encounters without perturbing its working performance. Handlers should be vigilant in identifying potential new distractions and incorporating those into their maintenance training activities.

Blank Searches

It is important for the search team to occasionally use a scenario in which there is no aid present. Should, in training, an aid always be found, the team, when conducting a search in which no aid is present, is able to become anxious and induce a false response. Since many actual searches result in no explosive present, the team should regularly train for blank searches.

Maintenance Training

Upon successful completion of basic training, the team should continue with regularly scheduled and ongoing maintenance training. The maintenance training, continued for the life of the working team, maintains competence in basic principles and allows the team to develop in those areas in which they are operational.

Each training session has specific goals—each session is carefully planned to meet specific objectives. This ongoing training is important for the continued effectiveness and success of the team.

In some embodiments, the training is conducted at least three times weekly with two of the sessions being devoted to Vapor Wake Screening.

The maintenance training should include training at actual deployment sites to further learn about air currents, human traffic flow and best practices for deployment. The maintenance training should also include new or unknown areas to the team allowing them to practice the best option for deployment.

In some embodiments, the team includes a canine, a handler and one or more spotters. The spotter is a person who trains regularly with the canine team and is familiar with the canine team operation. The spotter surveys the crowd and environment and assists the handler in deployment of the canine.

Documentation

Training is documented. The more detail, the better since it is able to assist a user in determining future training objectives and scenarios. Aspects of the training program should be varied, and good documentation helps vary these aspects by providing a user with something to look back at when planning the next training session. If areas, days, times, explosives, quantities or other items are repeated too frequently, the user should change so that the canine is not inadvertently learning aspects not desired to be learned. In some embodiments, at a minimum, the following should be documented:

1. Date/Time/Location of training.
2. Explosives—types and quantities.
3. Packaging of explosive training aid.
4. Sniff time—how long a dog works before detecting an explosive and each subsequent explosive if additional training aids are used.
5. Deficiency—identify any training deficiency the canine has that prevents it from performing at peak levels.
6 Corrective action—if a training deficiency is identified, a correct action for future training sessions is developed.
7. Follow-up training—describing how the corrective action is working to remedy the deficiency.

FIG. 1 illustrates a flowchart of a method of training a team in vapor wake detection according to some embodiments. In some embodiments, a canine is first selected based on demonstrating a high level of independent search behavior. In the step 100, training planning occurs. Training planning includes determining the type of vapor wake screening such as choke point, crowds, people moving and people standing still. Training planning also includes determining air currents throughout the area and determining if any air currents are to be manipulated (e.g. with a fan). In the step 102, the canine learns vapor wake detection techniques. The vapor wake detection techniques include learning to sample air currents. The vapor wake detection techniques include learning that the target odor is not limited to stationary objects, identifying a moving target and learning to follow the moving target. Following the moving target also includes pursuing the target from behind at a distance determined by the handler. The vapor wake detection techniques also include giving a final response (e.g. sitting). The canine is rewarded for performing correctly. In some embodiments, rewarding the canine includes a training perpetrator turning around to face the dog, removing a hidden reward and tossing the reward into the canine's mouth. The training sessions vary in time and odors. The training perpetrator is varied also. For example, the training perpetrator characteristics vary such as size, race and gender. In some training, distractions are implemented. The distractions are able to be any distractions such as blanks and distracting sights, sounds and circumstances. In some embodiments, documenting is utilized to track progress and retain other information. In some embodiments, maintenance training is implemented to hone the team's skills. Maintenance training includes focusing on deficiencies and addressing them. Each maintenance training session has specific goals that the team attempts to meet. The maintenance training occurs at actual deployment sites and/or new or unknown areas to further practice. Although specific steps are described, in some embodiments, fewer or more steps are included, and/or the order of the steps is able to be changed.

Figure 2:
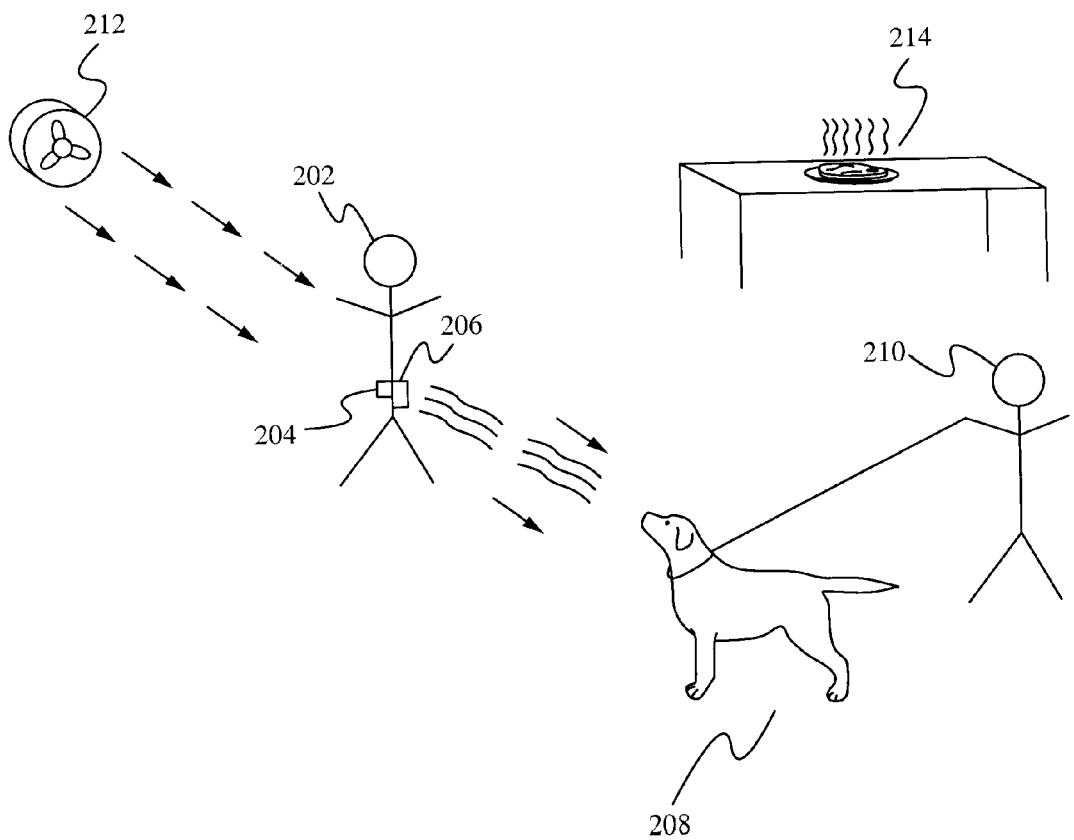
FIG. 2 illustrates a diagram of a training system according to some embodiments.

FIG. 2 illustrates a diagram of a training system according to some embodiments. In the training system 200, a training perpetrator 202 has a hidden reward 204 as well as a detectable item 206 to be detected such as an explosive. A canine 208 with a handler 210 train to implement vapor wake detection with the training perpetrator 202. After careful planning, the canine 208 and handler 210 are positioned appropriately to detect the scent of the detectable item 206. Appropriate positioning is such that the air flows to that area, and the canine is able to detect a scent. In some embodiments, a fan 212 or other device manipulates the air flow. The positioning is also based on the features of the location such as whether there is a choke point, a large area of people or a line of people. As described herein, the canine and handler position themselves appropriately depending on the situation to maximize the air flow and scents that the canine is able to analyze. Once the canine 208 detects the scent of the item 206, the canine 208 follows the protocol and follows the training perpetrator 202 and the item 206 until the appropriate time to give the final response. The handler 210 ensures the canine 208 stays at the appropriate distance. Once the final response is given, the training perpetrator 202 gives the canine 208 the hidden reward 204. Other training features are able to be implemented as well, such as distractions 214 or the training perpetrator 202 does not have the detectable item 206. Any other variations or features are able to be implemented in the training sessions.

Figure 3:
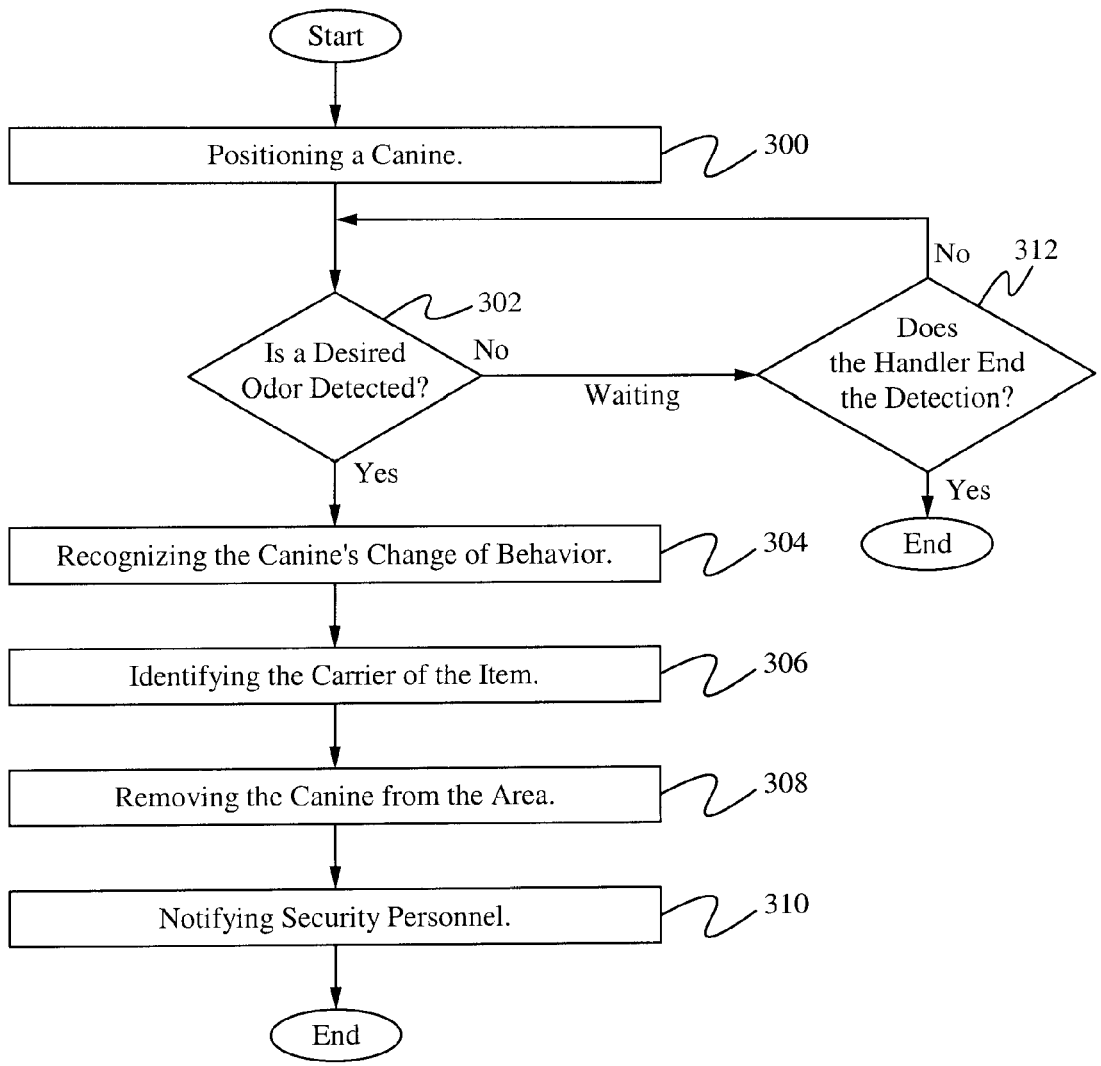
FIG. 3 illustrates a flowchart of a method of utilizing vapor wake detection according to some embodiments.

FIG. 3 illustrates a flowchart of a method of utilizing vapor wake detection according to some embodiments. In the step 300, a canine is positioned in an area that compliments vapor wake screening depending on the scenario. As described, the scenario is able to be people walking or standing, lines of people or people walking through a choke point, among other possible scenarios. In the step 302, if a desired odor (e.g. explosive) is detected, the canine follows behind the carrier of the item or approaches a stopped carrier of the item. In the step 304, the handler recognizes the canine's change in behavior. In the step 306, the handler identifies the carrier of the item. In some embodiments, in the step 308, the handler removes the canine from the area. The canine is removed any time before the final response. In the step 310, the handler notifies security personnel to take the appropriate action such as follow and observe or apprehend the person. If a desired odor is not detected, the canine continues to wait until a desired odor is detected or the handler ends the detection, in the step 312. Although specific steps are described, in some embodiments, fewer or more steps are included, and/or the order of the steps is able to be changed.

Figure 4:
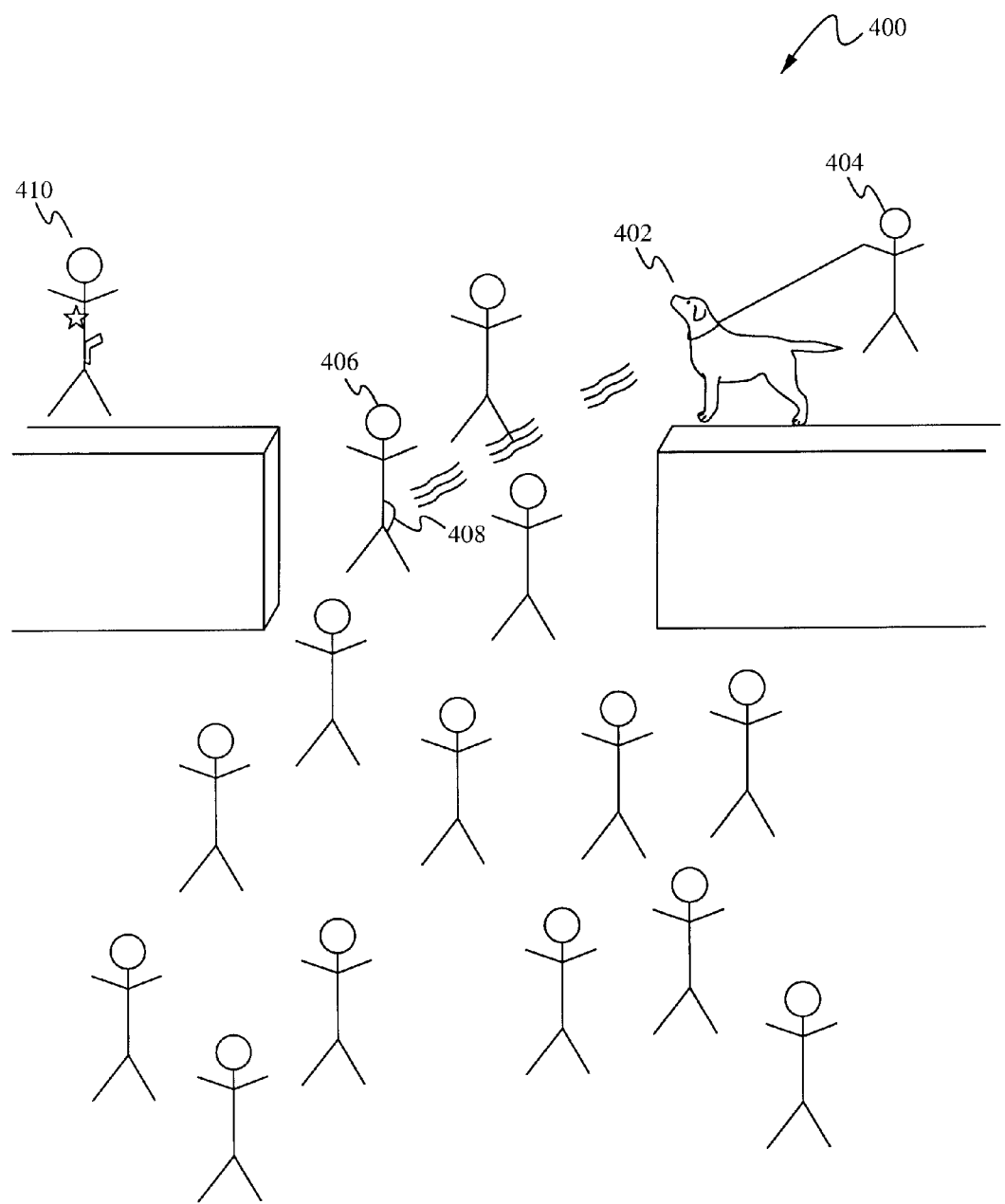
FIG. 4 illustrates a diagram of a vapor wake detection system according to some embodiments.

FIG. 4 illustrates a diagram of a vapor wake detection system according to some embodiments. The vapor wake detection system 400 includes a canine 402 and a handler 404. The canine 402 and the handler 404 are positioned properly so that the canine 402 is able to detect specific vapors such as bomb scents. In the example shown, the canine 402 and the handler 404 are positioned at a choke point. Once the canine 402 detects a target vapor, the canine 402 and the handler 404 follow the person 406 who has the item 408 emitting the vapor. The handler 404 determines who has the item 408 and contacts law enforcement personnel 410 to follow and/or apprehend the person 406. A fan (as shown in FIG. 2) is able to be used to direct air currents in a specified manner if desired. In some embodiments, the canine 402 and the handler 404 appear as law enforcement for a deterrent effect. In some embodiments, the canine 402 and the handler 404 appear without law enforcement uniforms such as a blind person and a seeing-eye dog to covertly detect illegal substances.

To utilize the dynamic canine tracking method, training is performed initially. The training includes determining a canine appropriate for training, preparing a training plan and having the canine learn to detect target odors, follow the carrier of the odor and take an action such as sitting when the carrier is identified. Then, once the training is completed, the canine is utilized by placing the canine in an appropriate location (e.g. near a choke point), allowing the canine to sniff the air attempting to detect a specified odor, following a carrier of the item emitting the odor, identifying the carrier and contacting the appropriate personnel to monitor and/or apprehend the carrier.

In operation, the method is a "dog-driven" detection method which is distinguished from traditional canine detection methods which are "handler driven." The method is referred to as Vapor-wake Detection. Some features of this method include the ability to screen large numbers of persons passing through a given space without affecting the throughput of the persons through the space and dogs are able to overcome distractions such as noise, commotion and ancillary environmental odors, to prevent loss of tracking of the target odorant. Applications of the methodology include the interdiction and capture of suicide bombers, narcotics handlers and purveyors or illicit chemical/biological warfare materials. The methodology is able to be applied in varied environments such as transit systems, venues for large public even gatherings such as stadiums and buildings and areas of commerce such as shopping malls and military environments.

The present invention has been described in terms of specific embodiments incorporating details to facilitate the understanding of principles of construction and operation of the invention. Such reference herein to specific embodiments and details thereof is not intended to limit the scope of the claims appended hereto. It will be readily apparent to one skilled in the art that other various modifications may be made in the embodiment chosen for illustration without departing from the spirit and scope of the invention as defined by the claims.

What is claimed is:

1. A method of training a canine for detection, the method comprising:
   choosing a detector canine that demonstrates a high level of independent search behavior;
   teaching the detector canine that a source of a target odor is not limited to stationary objects, and teaching the detector canine to not search stationary objects, wherein the source of the target odor is a hazardous or illicit substance;
   teaching the detector canine to follow a vapor-wake of a moving target, wherein the vapor-wake includes the target odor of the moving target;
   teaching the detector canine to sample air currents; and
   teaching the detector canine to follow the vapor-wake to the target and give a final response.

2. The method of claim 1, wherein the choosing of the detector canine that demonstrates a high level of independent search behavior further includes choosing the canine that is motivated, to sniff and search independently in a manner to disguise a handlers.

3. The method of claim 1, wherein the choosing of the detector canine that demonstrates a high level of independent search behavior further includes choosing the canine that is not overly sociable.

4. The method of claim 1, wherein the method further includes teaching the detector canine to search the air for a vapor trail or a scent pool of the target odor generated by the moving or stationary target.

5. The method of claim 1, wherein the method further includes teaching the detector canine to accommodate dissipation of the target odor over time.

6. The method of claim 1, further comprising teaching the detector canine to lead a handler to the source of the target odor, where the source of the target odor comes within a detectable range of the detector canine.

7. The method of claim 1, further comprising documenting the detector canine's sniffing capabilities.

8. The method of claim 7, further comprising choosing the detector canine that passes a medical examination.

9. The method of claim 8, wherein the medical examination includes testing for dexterity and freedom from bone, joint and musculature pathologies.

10. A method of training a detector canine that is not overly sociable and demonstrates a high level of independent search behavior, the method comprising:
    teaching the detector canine that a source of a target odor is not limited to stationary objects, and teaching the detector canine to not search stationary objects, wherein the source of the target odor is a hazardous or illicit substance;
    teaching the detector canine to follow a vapor-wake of a moving target, wherein the vapor-wake includes the target odor of the moving target;
    teaching the detector canine to sample air currents; and
    teaching the detector canine to search the air for vapor trails or scent pools of the target odor generated by a moving or stationary target.

11. The method of claim 10 further comprising teaching the detector canine to lead a handler to the source of the target odor, where the source of the target odor comes within a detectable range of the detector canine, and give a final response.

12. The method of claim 10 further comprising teaching the detector canine to follow the vapor-wake to the target and give a final response.

\* \* \* \* \*